United States Patent
Ghosh et al.

(10) Patent No.: US 6,498,038 B1
(45) Date of Patent: Dec. 24, 2002

(54) LOSS OF SIALIC ACID FROM APOLIPOPROTEIN J AS AN INDICATOR OF ALCOHOL INTAKE AND/OR ALCOHOL RELATED LIVER DAMAGE

(75) Inventors: Pradeep Ghosh, Gaithersburg, MD (US); Raj Lakshman, Bethesda, MD (US); Eric Anthony Hale, Baltimore, MD (US)

(73) Assignee: Bioprobes, Inc., Gathersburg, MD (US)

( * ) Notice: Subject to any disclaimer, the term of this patent is extended or adjusted under 35 U.S.C. 154(b) by 0 days.

(21) Appl. No.: 09/483,019

(22) Filed: Jan. 13, 2000

Related U.S. Application Data

(63) Continuation of application No. PCT/US98/14501, filed on Jul. 15, 1998.
(60) Provisional application No. 60/055,697, filed on Jul. 15, 1997.

(51) Int. Cl.$^7$ .......................... G01N 33/52; G01N 33/66; G01N 33/68
(52) U.S. Cl. ........................... 436/71; 436/87; 436/13; 436/15; 436/174; 436/175; 436/177; 436/178; 436/811; 436/538; 435/7.1; 435/7.92; 435/7.94; 530/412; 530/413; 530/417
(58) Field of Search .................. 435/2, 4, 6, 7.1, 435/7.8, 7.91, 7.92, 41, 87, 101, 268, 274; 436/63, 871, 71, 94, 96, 102, 13, 66, 175, 174, 519, 521, 538, 541, 548, 177, 178; 530/412, 413, 417; 536/127

(56) References Cited

U.S. PATENT DOCUMENTS

| | | | |
|---|---|---|---|
| 4,444,879 A | 4/1984 | Foster et al. | 435/7.2 |
| 4,626,355 A | 12/1986 | Joustra et al. | 210/635 |
| 5,296,346 A * | 3/1994 | Katopodis | 435/4 |
| 5,352,616 A | 10/1994 | Sunrehagen | 436/501 |
| 5,432,059 A | 7/1995 | Bean et al. | 435/15 |
| 5,702,904 A | 12/1997 | Makhlouf et al. | 435/7.1 |
| 5,712,157 A | 1/1998 | Marcovina et al. | 435/337 |
| 5,788,645 A * | 8/1998 | Jeppsson | 210/635 |
| 5,856,298 A * | 1/1999 | Strickland | 514/8 |
| 6,054,322 A * | 4/2000 | Sillanaukee et al. | 436/93 |
| 6,107,045 A * | 8/2000 | Koren et al. | 435/7.1 |
| 6,136,545 A * | 10/2000 | Hosel et la. | 435/7.1 |
| 6,136,960 A * | 10/2000 | Chait et al. | 530/412 |

FOREIGN PATENT DOCUMENTS

| | | | | |
|---|---|---|---|---|
| WO | WO 90/10225 | * | 9/1990 | 435/4 |
| WO | WO 92/08976 | | 5/1992 | |
| WO | WO 95/33993 | | 12/1995 | |

OTHER PUBLICATIONS

Burkey et al., Intracellular processing of Apolipoprotein J precursor to the mature heterodimer, Journal of Lipid Research 32(6): 1039–1048 (Jun. 1991) Abstract.*

Ghosh et al., Long Term Ethanol Impairs Glycosylation Of Both N– And O–Glycosylated Proteins In Rat Liver, Metabolism 44(7):890–98 (1995).

Ghosh et al., Effects Of Chronic Ethanol on Enzymes Regulating Sialylation And Desialylation Of Transferrin In Rats, Alcoh. Clin. Exp. Res. 17(3):576–79 (1993).

(List continued on next page.)

Primary Examiner—Long V. Le
Assistant Examiner—Gailene R. Gabel
(74) Attorney, Agent, or Firm—Gary Pisner

(57) ABSTRACT

Disclosed is a method for determining alcohol intake or alcohol induced liver damage in a subject by quantifying the content of sialic acid in apolipoprotein J (Apo J). In particular the present invention involves the steps of (a) providing a sample containing Apo J from a subject; (b) purifying the Apo J from the sample; (c) determining sialylation index, i.e., moles of sialic acid peer mole of Apo J in the sample; and (d) evaluating whether the sialylation index is an indication of alcohol intake or alcohol related liver damage recovery from alcohol addiction or alcohol relapse in the subject.

19 Claims, 3 Drawing Sheets

OTHER PUBLICATIONS

Stowell et al., Comparison Of Two Commercial Test Kits For Quantification Of Serum Carbohydrate–Deficient Transferrin, Alcoh. Alcoh. 32(4):507–16 (1997).

Lesch et al., Alcohol Dependence: Is Carbohydrate–Deficient Transferrin A Marker For Alcohol Intake? Alcoh. Alcoh. 31(3):257–64 (1996).

Lesch et al., Carbohydrate–Deficient Transferrin As A Marker Of Alcohol Intake: A Study With Healthy Subjects, Alcoh. Alcoh. 31(3):265–71 (1996).

de Silva et al., Apolipoprotein J: Structure And Tissue Distribution, Biochem. Biochem. 29:5380–89 (1990).

de Silva et al., Purification And Characterization Of Apolipoprotein J, J. Biol. Chem. 265(24):14292–97 (1990).

Collard, M.W. & Griswold, M.D., Biosynthesis And Molecular Cloning Of Sulfated Glycoprotein 2 Secreted By Rat Sertoli Cells, Biochem. 26:3297–03 (1987).

Warren, L., The Thiobarbituric Acid Assay Of Sialic Acids, J. Biol. Chem. 234(8):1971–75 (1959).

Hogan, I.E., A Modified Spectrophotometric Method For Determination Of Nanogram Quantities Of Sialic Acid, Clin. Chem. Acta 116:409–15 (1981).

Lowry et al., Protein Measurement With The Folin Phenol Reagent, J. Biol. Chem. 193:265–75 (1951).

Bradford, M.M., A Rapid And Sensitive Method For Quantiation Of Microgram Quantities Of Protein Utilizing The Principle Of Protein–Dye Binding, Anal. Biochem. 72:248–54 (1976).

Burstein et al., Rapid Method For The Isolation Of Lipoproteins From Human Serum By Percipitation With Polyanions, J. Lipid Res. 11:583–89 (1970).

Smith et al., Measurement Of Protein Using Bicinchoninic Acid, Anal. Biochem. 150:76–85 (1985).

Cottalasso et al., Effect Of Ethanol Administration On The Level Of Dilichol In Rat Liver Microsomes And Golgi Apparatus, Alcoh. Clin. Exp. Res. 22(3):730–37 (1998).

Xin et al., Serum Carbohydrate–Dificient Transferrin: Mechanism Of Increase After Chronic Alcohol Intake, Hepatol. 22:1462–68 (1995).

Ghosh, P. & Lakshman, M.R., Chronic Ethanol Induced Impairment Of Hepatic Glycosylation Machinery In Rat Is Independent Of Dietary Charbohydrate, Alcoh. Clin. Exp. Res. 21(1):76–81 (1997).

Anton et al., Biological Assessment Of Alcohol Comsumption.

Salomaki, P, et al. Prenatal Detection of Free Sialic Acid Storage Disease: Genetic And Biochemical Studies In Nine Families Abstract Prenat Diagn May 2001, 21(5):354–358.

Tanaka, F, et al. Prognostic Significance Of Polysialic Acid Expression In Resected Non–Small Cell Lung Cancer Abstract Cancer Res Feb. 2001 15,61(4) 1666–70.

Wang, S., et al. Reduction In Cholesterol And Sialic Acid Content Protects Cells From The Toxic Effects Of Beta–Amyloid Peptides Abstract J.Biol. Chem. Sep. 13, 2001.

Carbillon, L, et al. Ultrasound Assessment In A Case Of Sialic Acid Storage Disease Ultrasound Abstract Obstet Gynecol Sep. 2001;18(3) 272–4.

Crook, MA, et al, Relationship Between Plasma Sialic Acid Concentration And Microvascular And Microvascular Complications In Type 1 Diabetes: The Eurodiab Complications Study. Abstract Diabetes Care Feb. 2001;24(2):316–22.

Gokmen, SS, et al. Serum Total And Lipid–Bound Sialic Acid Levels Following Acute Myocardial Infarction, Abstract Clin Chem Lab Med Dec., 2000 38(12):1249.

Szprynger, K, et al. Evaluation Of Serum Sialic Acid Concentration In Chronic Renal Failure Children On Continuous Ambulatory Peritoneal Dialysis And Hemodialysis Abstract Pol Merkuriusz Lek Jul. 2000;8(49):459–61.

Sonmez, H, et al. Carbohydrate–Deficient Transferrin And Sialidase Levels In Coronary Heart Disease, Abstract Thromb Res Aug. 15, 2000 99(4):311–5.

Brochez, L, et al. Serological Markers For Melanoma Abstract Br J Dermatol Aug. 2000;143(2):256–68.

Lindbohm, N Sialic Acid Content Of Low–Density Lipoprotein In Women With Coronary Artery Disease Abstract J Lab Clin Med Aug. 2000;136(2):110–5.

Abdella, N Relation Of Serum Total Sialic Acid Concentration With Diabetic Complications And Cardiovascular Risk Factors In Kuwaiti Type 2 Diabetic Patients Abstract Diabetes Res Clin Pract Sep. 2000;50(1):65–72.

Nozawa, Y, et al. Distribution Of Sialic Acid–Dependent Carbohydrate Epitope In Thyroid Tumors: Immunoreactivity of FB21 In Paraffin–Embeded Tissue Sections. Abstract Pathol. Int. May 1999, 49(5):403–7.

Fujita, T, et al. Inhibitory Effect Of Free Sialic Acid On Complement Activation And Its Significance In Hypocomplementemic Glomerulonephritis Abstract J Clin. Lab. Anal. 1999;13(4):173–9.

Schmid,JA, et al. Accumulation Of Sialic Acid In Endocytic Compartments Interferes With The Formation Of Mature Lysosomes, Impaired Proteolytic Processing Of Cathepsim B In Fibroblasts Of Patients With Lysosomal Sialic Acid Storage Disease Abstract J. Biol. Chem. Jul. 1999 2;274(27):19063–71.

Gabrielyan, ND, et al. Investigation Of Sialic Acids And Sialyltransferase Activity In Blood Of Patients With Systemic Scleroderma Abstract Biochemistry (MOSC) May 1999;64(5):561–4.

Chatterjee, M, et al. Identification Of Antibodies Directed Against O–Acetylated Sialic Acids In Visceral Leishmaniasis; Its Diagnostic and Prognostic Role Abstract Glycoconj. J. Dec. 1998;15(12):1141–7.

Sillanaukee, P, et al. Occurrence Of Sialic Acids In Healthy Humans And Different Disorders Abstract Eur J Clin Invest May 1999;29(5):413–25.

Inoue, T, et al. Structural Studies Of Sugar Chains Of Carbohydrate–Deficient Transferrin From Patients With Alcoholic Liver Disease Using Lectim Affinity Electrophoresis Abstract Electrophoresis Mar. 1999;20(3):452–7.

Takahashi, S, et al. Capsular Sialic Acid Limits C5A Production On Type III Group B Streptococci Abstract Infect. Immun. Apr. 1999 L67(4):1866–70.

Hobarth, K, et al. Plasma Sialic Acid In Patients With Prostate Cancer Abstract Br. J. Urol. Nov. 1993;72(5PT 1):621–4.

Lemyre, E, et al. Clinical Spectrum Of Infantile Free Sialic Acid Storage Disease Abstract Am. J. Med. Genet. Feb. 1999 19;82(5):385–.

Suhonen–Polvi, H, et al. Increased Brain Glucose Utilization In Salla Disease (Free Sialic Acid Storage Disorder) Abstract J. Nucl. Med. Jan. 1999;40(1);12–8.

Lindbohm, N, et al. Sialic Acid Content Of Low Density Lipoprotein And Its Relation To Lipid Concentrations And Metabolism Of Low Density Lipoprotein And Cholesterol Abstract J. Lipid. Res. 2000; 41(7):1110–7.

Tanaka, F, et al. Expression Of Polysialic Acid And STX, A Human Polysialytransferase, Is Correlated With Tummer Progression In Non–Small Cell Lung Cancer Abstract Cancer Res. Jun. 1, 2000 60(11):3072–80.

Fernandes–Rodriguez, J, et al. Immunohistochemical Analysis Of Sialic Acid And Fucose Composition In Human Colorectal Adenocarcinoma Abstract Tummer Biol. May–Jun. 2000, 21(3):153–64.

Kalela, A, et al. Association Of Serum Sialic Acid And MMP–9 With Lipids And Inflammatory Markers Abstract Eur. J. Clin. Intest. Feb. 2000, 30(2):99–104.

Penaloza, A, et al Sialic Acid Residues In The Labial Salivary Glands From Sjogren's Syndrome Patents Abstract Clin. Exp. Rheumatol. Nov.–Dec. 1999, 17(6):713.

Lefebvre, G, et al. Recurrent Nonimmune Hydrops Fetalis: A Rare Presentation Of Sialic Acid Storage Disease Abstract Genet. Couns. 1999, 10(3):277–84.

Ponnio, M, et al. Serum Sialic Acid In A Random Sample Of The General Population Abstract Clin. Chem Oct. 1999;45(10) 1842–9.

Wu, EB, et al. Plasma Sialic Acid And Coronary Artery Atheromatous Load In Patents With Stable Chest Pains Abstract Atherosclerosis Aug. 1999; 145(2) 261–6.

Lindberg, G Serum Sialic Acid And Sialoclycoproteins In Asymptomatic Carotid Artery Atherosclerosis, Aric Investigators, Atherosclerosis Risk In Communities Abstract Atherosclerosis Sep. 1999;146(1):65–9.

Lindbohm, N, et al. Sialic Acid Content Of LDL And Lipoprotein Metabolism In Combined Huperlipidemia And Primary Moderate Hypercholesterolemia Abstract Clin Chim Acta Jul. 1999; 285(1–2):69–84.

Christ, ER, et al. Growth Hormone (GH) Replacement Therapy Reduces Serum Sialic Acid Concentrations In Adults With GH–Deficiency: A Double–Blind Placebo–Controlled Study Abstract Clin. Endocrinol.(OXF) Aug. 1999;51(2):173–9.

Thougaard, AV, et al. Total Serum Sialic Acid Is A General Disease Marker Rather Than A Specific Tumor Marker In Dogs Abstract Zentralbl Veterinarmed. A Oct. 1998;45(8):471–9.

Masuda, H, et al. Serum Sialic Acid And Ankle Versus Brachial Arterial–Pressure Rato In Niddm Abstract Scand. J. Clin. Lab. Invest. Aug. 1998;58(5):433–39.

Salomone OA, et al. Serum Sialic Acid Conentration Is Not Associated With Extent Or Severity Of Coronary Artery Disease In Patients With Stable Abstract Am. Heart J. Oct. 1998;136(4 pT 1):620–3.

Inoue, S, et al. Identification Of Free Deaminated Sialic Acid (2–Keto–3–Deoxy–D–Glycero–D–Galacto–Nononic Acid) In Human Red Blood Cells And Its Elevated Expression In Fetal Cord Red Blood Cells And Ovarian Cancer Cells Abstract J. Biol. Chem. Oct. 1998 16;273(42):27199–204.

Chappey, B, et al. Sialic Acid Content Of LDL In Coronary Artery Disease No Evidence Of Desialylation In Subjects With Coronary Stenosis And Increased Levels In Subjects With Extensive Atherosclerosis And Acute Myocardial Infarction: Relation Between Desilaylation And In Vitro Peroxidation Abstract Arterioscler. Thromb. Biol. Jun. 1998 18;(6):876–83.

Rao, VR , et al. Circulating Levels In Serum Of Total Sialic Acid, Lipid–Associated Sialic Acid, And Fucose In Precancerous Lesion And Cancer Of The Oral Cavity Abstract Cancer Detect Prev 1998:22(3):237–40.

Bircan, Z, et al. Sialic Acid In Childhood Renal Diseases: Correlation With Clinical And Laboratory Indices Abstract Acta. Paediatr. Jpn Feb. 1998;40(1):65–9.

Cojocaru, M, et al, Relationship Between Serum Total Sialic Acid And C–Reactive Protein In Silicosis Abstract Rom. J. Intern. Med. Jan.–Dec. 1997;35(1–4):77–82.

Crook, M, et al. Serum Sialic Acid, A Reputed Cardiovascular Risk Factor, Is Elevated In South Asian Men Compared To European Men Abstract Ann. Clin. Biochem Mar. 1998;35 (PT2):242–4.

Shakshikanth, MC, et al. Study Of Serum Fucose And Serum Sialic Acid Levels In Oral Squamous Cell Carcinomia Abstract Indian J. Dent. Res. Oct.–Dec. 1994;5(4):119–24.

Paszkowska, A, et al. Sialic Acid Concentration In Serum And Tissue Of Endometrial Cancer Patients Abstract Eur. J. Obstet. Gynecol. Reprod. Biol. Feb. 1998;76 (2):211–5.

Crook, M, et al. The Relationship Between The Female Menopause And Serum Sialic Acid, A Known Cardiovascular Risk Factor Abstract Eur. J. Obstet. Gynecol. Reprod. Biol. Feb. 1998;76 (2):185–7.

Painbeni, T, et al. Plasma Sialic Acid As A Marker Of The Effect Of The Treatment On Metastatic Colorectal Cancer Abstract Eur. J. Cancer Nov. 1997;33(13):2216–20.

Tomaszewska, R, et al. Sialic Acid Concentration In Different Stages of Malignant Lymphoma And Leukemia In Children Abstract Acta. Paediatr. Jpn. Aug. 1997;39(4):448–50.

* cited by examiner

LOSS OF SIALIC ACID FROM APOLIPOPROTEIN J AS AN INDICATOR OF ALCOHOL INTAKE AND/OR ALCOHOL RELATED LIVER DAMAGE

CROSS-REFERENCE TO RELATED APPLICATIONS

This application is entitled to the priority benefit of provisional patent No. 60/055,697 filed Jul. 15, 1997 (ABANDONED) and is a continuation of PCT application number PCT/US98/14501 filed Jul. 15, 1998, now WO 99/04260.

TECHNICAL FIELD

The present invention relates to a method for detecting pathological and metabolic changes related to alcohol intake in an individual, and more particularly to a method for detecting alcohol intake and alcohol related liver damage by measuring the sialylation index of apolipoprotein J.

BACKGROUND ART

There are about 10 million alcoholics in the United States. Alcoholic liver disease is a major cause of morbidity and mortality in the United States and in many other countries in the world. Ethanol is toxic to the liver. Thus, the persistent, excessive intake of ethanol can lead to a number of complications in the human body, including damage to liver cells and eventually, to cirrhosis of the liver.

Profound changes in the concentration and composition of plasma lipids and lipoproteins occur at each stage of excessive alcohol intake and/or alcohol-induced liver injury. Ghosh, P. et al., "Long-Term Ethanol Exposure Impairs Glycosylation of Both N— and O— Glycosylated Proteins in Rat Liver," Metabolism 44: 890–898 (1995). One of the main sites of ethanol attack is the glycosylation machinery of the liver. This deleterious action of ethanol manifests itself by altering specific activities of the sialylation and desialylation enzymes of the liver which results in either defective sialylation of proteins or increased hydrolysis of molecules that eventually result in the depletion of sialic acid residues from sialylomolecules. See Ghosh, P. et al., "Effects of Chronic Ethanol on Enzymes Regulating Sialylation and Desialylation of Transferrin in Rats," Alcoh. Clin. Exp. Res. 17: 576–579 (1993). Hepatocellular degeneration results in a variety of clinical symptoms ranging from a relatively asymptomatic enlargement of the liver to massive fatty infiltration. As the alcohol abuse continues, these degenerative processes manifest themselves into liver dysfunction, chronic inflammation, and structural distortion of cells leading to proliferation of fibrous tissue, and ultimately to cirrhosis and necrosis of the liver. Total hepatic failure and death may occur as a result of prolonged alcohol abuse in humans.

Self-reporting of alcohol intake is unreliable. Accordingly, tests to diagnose alcohol intake have been developed. Serum carbohydrate-deficient transferrin (CDT) is considered to be a viable marker for alcohol intake. Transferrin is a sialoglycoprotein that transports iron into cells and is present at high concentrations in serum. Excessive alcohol intake by an individual, or ingestion of greater than 60 grams of ethanol daily, produces high levels of CDT in serum. Normal individuals and non-alcoholic liver disease patients do not exhibit the elevation of CDT (except in a few primary biliary cirrhosis or hepatitis).

Tests based on the CDT marker are generally directed to identifying and quantifying CDT in a sample. U.S. Pat. No. 4,626,355 discloses a method for determining the alcohol intake in an individual by quantifying the isotransferrins (CDT) in the individual's body fluids. The method taught in U.S. Pat. No. 5,432,059 entails detecting CDT by reglycosylating (with a fluorescent-conjugate) deglycosylated glycoproteins in a sample; detecting the fluorescent, reglycosylated glycoprotein using a flurometer; and quantifying the amount of reglycosylated glycoproteins in a sample. U.S. Pat. No. 5,702,904 discloses a CDT based immunoassay which utilizes an antibody that reacts specifically with CDT.

The CDT tests are laborious, time consuming and expensive. More importantly, the validity of the CDT marker has been seriously questioned. In fact, the CDT marker has been reported to be invalid in alcoholics who consume less that 60 grams of alcohol per day, pregnant women, and in patients with hepatitis. See Stowell, L. I. et al., "CDT test is not valid in detecting less excessive regular drinking in young males and females,"Alcohol Alcohol 32: 507–517 (1997); Lesch, O.N. et al., "No correlation of CDT with alcohol-related disabilities, severity of withdrawal syndrome," Alcohol Alcohol 31: 257–264 (1996); Lesch, O. N. et al., "CDT not sensitive for short-term heavy drinking by healthy subjects," Alcohol Alcohol 31: 265–271 (1996). The result of a recent study conducted jointly by NIAAA, NHLBI and VA, showed that CDT levels were unaffected by as large as a 50% decrease in the amount of alcohol consumed by the study subjects. See Lakshman, R., A report submitted to the NIH by Study Director Raj Lakshman, Ph.D. (personal communication). Therefore, a cost-effective and reliable marker for alcohol intake and alcohol related liver damage is still needed for early diagnosis and treatment of alcoholism and related liver damage.

SUMMARY OF THE INVENTION

One aspect of the present invention is directed to a method for detecting alcohol intake and alcohol related liver damage in an individual, which involves the following steps:

a. providing a sample containing Apolipoprotein J (Apo J);

b. purifying the Apo J;

c. determining sialic acid content of the purified Apo J relative to protein content of Apo J in the sample; and d. evaluating whether the sialylation acid index of Apo J is an indication of alcohol intake or alcohol related liver damage in the subject, or the extent of detoxification or recovery from alcohol related illness.

In preferred embodiments, the Apo J protein is purified via immunoaff inity chromatography matrix, such as a column comprising immobilized antibodies that specifically bind Apo J. The Apo J sample is obtained in blood, serum, plasma or high density lipoprotein (HDL). The sialic acid content is determined by subjecting the purified Apo J to acid hydrolysis to release the sialic acid residues from the apolipoprotein. The content of sialic acid is expressed in terms of a sialylation index (SI), i.e., moles of sialic acid per mole of Apo J protein. The SI ratio obtained is compared to a control or standard SI generated from non-drinkers as an indication of alcohol intake and/or liver damage.

Another aspect of this invention is directed to a kit for measuring the sialic acid content of Apo J. The kit contains a matrix having immobilized anti-Apo J antibodies and a desialylation agent. In preferred embodiments, the matrix is contained in a column, and the desialylation agent is an enzyme or acid such as sulfuric acid. In another preferred embodiment, the kit also contains a desalting column and washing and elution buffers.

Apo J is a 70 kilodalton apolipoprotein component of plasma high density lipoproteins. Applicant has discovered that the Apo J sialic acid test is more sensitive than the CDT test to changes in alcohol intake. In a side-by-side comparison, Applicant demonstrated that preferred forms of the present invention can provide as much as about 20% more sensitivity than tests based on the CDT marker. The present invention offers a better alternative to the CDT test because it is specific, sensitive, simple, and cost-effective.

DETAILED DESCRIPTION OF INVENTION

Figure 1:
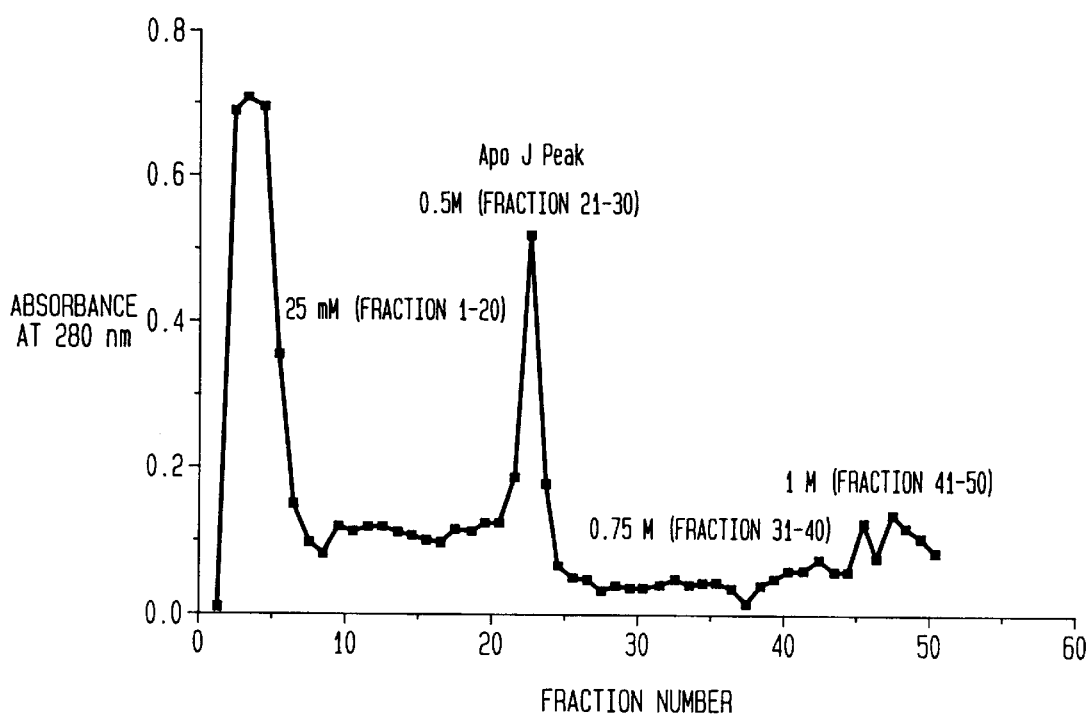
FIG. 1. is a graph which shows Apolipoprotein J purification through an anti-Apo J affinity column.

The nucleic acid sequence and corresponding amino acid sequence for Apo J is set forth in de Silva, H. V. et al., "Apolipoprotein J: Structure and Tissue Distribution," Biochemistry 29: 5380–5389 (1990) ("de Silva I"). Applicant has also surprisingly and unexpectedly determined that Apo J has seven times more sialic acid residues than transferrin.

By the term "sample," it is meant to include biological fluids such as blood, plasma, serum, and HDL, or any tissue that contains Apo J. The sample may be stored for a reasonable time prior to analysis. In general, the Apo J sample can be stored from about $-20°$ C. to about $-70°$ C. for at least about 30 days without affecting the recovery of Apo J. Temperatures above room temperature should be avoided, at least for plasma samples. Plasma samples, on the other hand, are preferably stored at $4°$ C.

To conduct the present method, the Apo J in the sample is purified. In the context of the present invention, "purified" means that the Apo J is isolated from other sialylated biomolecules that may be present in the sample to such a degree that the sialic acid content of any impurities is insignificant in comparison to Apo J sialic acid content of Apo J in the sample. Preferably any non-Apo J sialic acid content is less than 2% of the total sialic acid in the purified sample. More preferably, such isolation removes all other sialylated biomolecules. It is preferred, however, that Apo J is isolated to the extent of being a substantially homogenous protein. The purification of Apo J from a sample can be accomplished in accordance with standard purification techniques, such as immunoaffinity chromatography and reverse phase high-performance liquid chromatography (RP-HPLC). See de Silva et al., J. Biol. Chem. 24: 14292–14297 (1990) ("de Silva II"). In a preferred embodiment, Apo J is purified via immunoaffinity chromatography. In a more preferred embodiment, an affinity column having anti-human Apo J monoclonal antibodies immobilized thereon is employed. Anti-Apo J antibodies can be made following known procedures. See, e.g., de Silva II. Antibodies raised against Apo J are preferred. However, antibodies raised against the major rat Sertoli cell protein, sulfated glycoprotein 2 (SPG2) (see Collard, M. W. & Griswold, M. D., Biochemistry 26: 3297–3303) can also be used in view of the high degree of similarity as described in de Silva I and the absence of rat protein in humans.

Once purified Apo J is obtained, the sialic acid content is measured. In a preferred embodiment, this entails desialylating--that is, releasing the sialic acid residues from Apo J. This step is most easily performed by acid hydrolysis. Suitable hydrolysis techniques are chemical or enzymatic in nature. Suitable enzymes include the enzyme neuraminidase (Sigma Chemical). In a preferred embodiment, the desialylation step is performed using sulfuric acid at a normality of 0.1 as a hydrolyzing agent.

Determining the sialic acid content of Apo J can be accomplished using standard procedures. For example, the content of sialic acid in the Apo J fraction can be measured spectrophotometrically according to the method described in Warren, "The Thiobarbituric Acid Assay of Sialic Acid," J. Biol. Chem. 234: 1971–1975 (1959). The content of sialic acid in the Apo J fraction can also be accomplished using the modified method described by Horgan. Horgan, I. E., Clin. Chem. Acta. 116: 409–415 (1981). Sialic acid content is preferably expressed as a sialylation index (SI) defined as moles of sialic acid per mole of Apo J protein. Protein content in the Apo J fractions can be measured, for example, by using the Lowry Protein Assay. Lowry, H. L. et al. J. Biol. Chem. 193: 265–275 (1951). Other methods which may be used to measure protein content in the Apo J fraction include the Pierce Binchoninic, Bradford and BioRad methods. Bradford, M. M., Analytical Biochem. 72: 248–254 (1976).

Applicant has determined that the SI of Apo J in non-drinkers is about 28; the SI in moderate alcohol drinkers or individuals who consume between about 40 grams to about 60 grams of alcohol daily ranges from about 17 to about 19; and the SI in chronic alcohol drinkers or individuals who consume greater than 60 grams of alcohol on a daily basis ranges from about 12 to about 14. Evaluating, e.g., comparing, the sialylation index of Apo J to the standard or control will indicate the nature and amount of alcohol intake, alcohol-related liver damage or dysfunction. Control values can be generated simply by testing various classes of individuals in accordance with the presently disclosed methods. Applicant has also demonstrated the existence of a positive correlation between alcohol abuse or alcohol related liver damage and Apo J sialylation index in female subjects. Although Apo J levels tend to be higher in females as compared to males, the molar ratio of sialic acid content to that of Apo J protein remains the same in both males and females. Thus, unlike the CDT test, the present method is equally reliable for both males and females.

Another embodiment of the invention is directed to a kit for detecting the sialic acid content of Apo J. The preferred uses of the kit are to assess alcohol intake, alcohol related damage or dysfunction, or the extent of recovery or abstention of an individual in a detoxification program. The kit may also be used, however, in any application where sialic acid content of Apo J may be significant, particularly from a diagnostic standpoint.

The kit contains a matrix having immobilized thereon anti-Apo J antibodies and a desialylation agent. In preferred embodiments, the matrix is contained in a column, and the agent is an enzyme or acid. The antibodies may be either polyclonal or monoclonal and are specific to mammalian Apo J. Preferably the antibodies are specific to human Apo J In a more preferred embodiments, the kit contains two filtration columns for desalting a detergent agent to facilitate release of Apo J from HDL; anti-human Apo J for purifying the Apo J; washing buffers with different salt concentrations; and an elution buffer with a salt concentration of about 0.75 M NaCl.

In an even more preferred embodiment, the kit contains: (a) two Sephadex® G-25 columns (0.5 cm×2.5cm); (b)

detergent reagent (100 mM sodium deoxycholate solution); (c) anti-human Apo J (monoclonal) -Sepharose 4B column (0.5 cm×2.5 cm); (d) washing buffers (1–4); (e) elution buffer (5); (f) hydrolysis reagent (0.1 N sulfuric acid); (g) sialic acid measurement reagents: i. sodium arsenite, ii. sodium meta periodate, iii. thiobarbituric acid (TBA) solution; and (h) optimized standard solution of sialic acid (1 mg/13.3 mL). The HDL is preferably dialyzed against buffer overnight. The affinity chromatography is preferably carried out at 4° C. After loading the HDL sample, the affinity column should preferably be washed with washing buffer before eluting the purified Apo J with buffer.

The invention will be further described by reference to the following detailed examples. These examples are provided for purposes of illustration only, and are not intended to be limiting unless otherwise specified.

DETAILED DESCRIPTION OF THE PREFERRED EMBODIMENTS

EXAMPLE I

Purification of Human and Rat Plasma Apo J: Isolation and Characterization of HDL from Rat and Human Plasma A. Isolation of Plasma HDL HDL subfractions were isolated using heparin $MnCl_2$ and dextran sulfate-$MnCl_2$ as described in Burstein, M. et al., J. Lipid Res. 11: 583–589 (1970). The isolated HDL fractions were characterized and the purity and yield determined by their protein, and cholesterol content. Contamination of the lipoprotein fractions were checked by analytical SDS-PAGE.

B. Purification of Apoprotein J from isolated HDL fraction.

The HDL fraction was dissolved in sodium bicarbonate buffer (0.09 M, pH 8.3) and was extensively dialyzed against normal saline-EDTA for 24 hours. The dialyzed fraction was then incubated with sodium-deoxycholate (10 mM final concentration) at 37° for 1 hr. followed by incubation at 4° C., passed through Sephadex G-25 and passed through heparin-Sepharose column (10×0.5 cm) equilibrated with phosphate buffer (0.01 M, pH 7.4 with 0.01% cystine). The bound protein bands were then sequentially eluted with the same buffer containing 0.15 M, 0.25 M, 0.5 M, 0.75 M and 1.0 M NaCl. The collected fractions were then monitored at 280 nm for protein. The protein peak fractions were pooled, concentrated in a Speed-Vac concentrator, run through analytical PAGE along with markers and stained with silver-stain (BioRad). The fraction corresponding to a single band at 70 kD was eluted with the elution buffer containing 0.75 M NaCl. The authenticity of this protein to be Apo J was confirmed by Ouchterlony analysis using anti-Apo J.

C. Anti Apo J Antibody Production

Rabbits were immunized with repeated injections (every 2 weeks for 8 weeks) of pure human Apo J (1 mg/injection). At the end of 8 weeks, the plasma from both rabbits were tested for their specificity by Ouchterlony immunodiffusion analysis. It was demonstrated that the rabbit IgG for human Apo J cross-reacted only with human Apo J. There was no cross-reactivity to other antigens such as ApoE, ApoA and albumin.

D. Development of a Immunoaffinity anti-Apo J column

The IgG fraction of the rabbit antiserum for Apo J (0.5 ml equivalent of serum) was conjugated with CNBr activated Sepharose-4B beads (2.5 ml bed volume) according to manufacturer's instructions. It was found that 81% of the anti Apo J was tightly bound to the affinity matrix.

E. Specificity of the anti-Apo J column

The following steps were determined to be optimal for the affinity purification of Apo J from rat and human plasma.

i. precipitate LDL from 1 ml plasma with heparin-$MnCl_2$
  ii. precipitate HDL from LDL-free plasma with dextran sulfate-$MnCl_2$ reagent.
  iii. desalt by gel-filtration on Sephadex G-25 column using buffer 1 (10mM potassium phosphate buffer, pH 7.6 containing 25 mN NaCl).
  iv. dissociate HDL-complex by incubation initially at 37° C. and then overnight at 4° C. with 10 mM sodium deoxycholate followed by gel filtration on a Sephadex G-25 column. Elute the dissociated HDL fraction with buffer 1.

F. Purification of Apo J by affinity chromatography on Anti-Apo J column

Affinity chromatography was carried out at 4° C. After loading the dissociated HDL sample, Apo J was obtained from the affinity column after eluting sequentially with (a) 30 vol. of buffer 2 (10 mM potassium phosphate buffer, pH 7.6 containing 25 mM NaCl);
  (b) 10 vol. of buffer 3 (10 mM potassium phosphate buffer, pH 7.6 containing 500 mM NaCl);
  (c) 10 vol. of buffer 4 (10 mM potassium phosphate buffer, pH 7.6 containing 750 mM NaCl); and
  (d) 10 vol. of buffer 5 (10 mM potassium phosphate buffer, pH 7.6 containing 1000 mM NaCl).

A typical elution profile of pure Apo J from this affinity column is shown in FIG. 1. It was found that the protein fraction eluted with first 3 ml of buffer 3 was proven to be pure Apo J by PAGE and Ouchterlony analysis.

G. Validation of the quantitative recovery of plasma Apo J from anti-Apo J column.

Affinity chromatography of plasma HDL samples (1 ml plasma equivalent) from five control and five chronic alcohol-fed rats on Anti-Apo J column (0.5 cm×2.5 cm) gave consistently 41.8±4.2 μg and 42.3±5.1 μg, respectively. The mean rat plasma HDL Apo J value determined on the same above samples was 85 μg/ml.

Plasma Apo J sialic acid content from alcohol-fed animals was decreased by 44%. Under these experimental conditions, the recovery of plasma Apo J was 49–50% irrespective of variations in the amount of sialic acid in Apo J of these samples. These results demonstrate that the affinity of Apo J to Anti-J column is primarily due to the protein moiety and is unaffected by significant alteration in sialic acid content of Apo J.

H. The stability and storage of anti-Apo J columns The standard Anti Apo J columns (0.5 cm+2.5 cm) have been stored at 4° C. for more than 3 months and repeatedly (at least 6 times) used for the isolation of pure Apo J without any deterioration of their binding capacity or resolving power.

EXAMPLE II

Determination of Sialic Acid Content of Apo J

Figure 2:
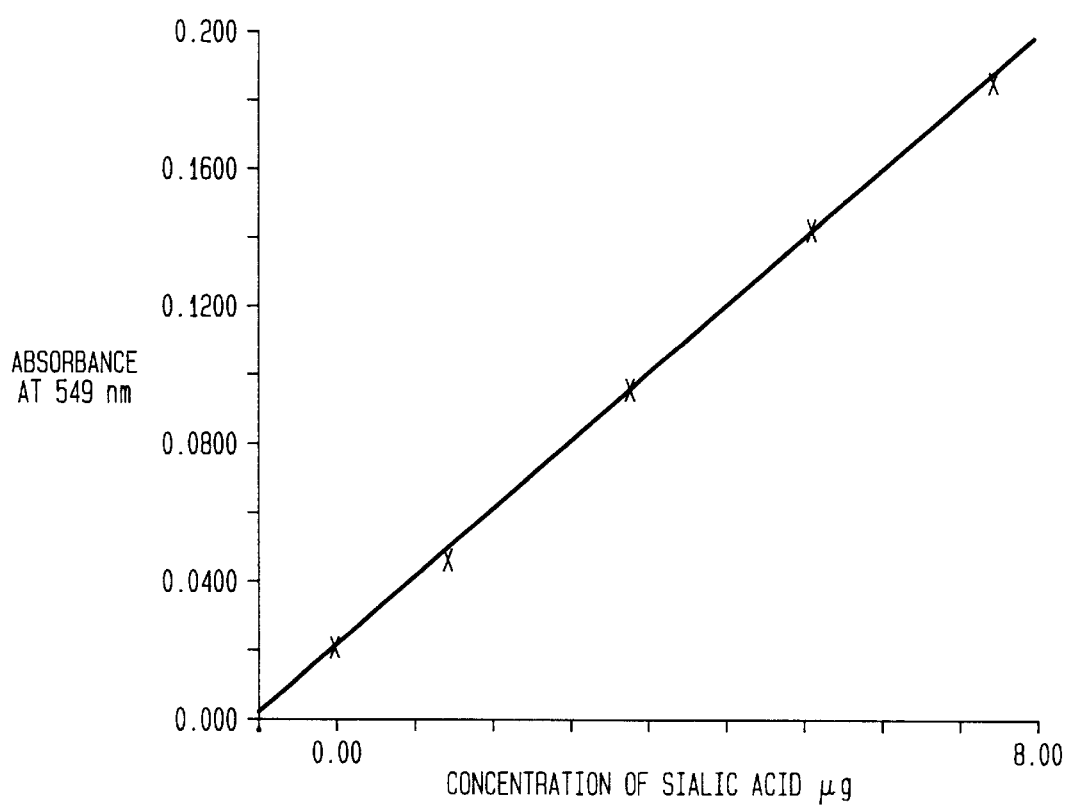
FIG. 2. is a graph of a thiobarbituriric acid assay which shows a typical sialic acid analysis standard curve.

Spectrophotometric method for the quantitative measurement of sialic acid was validated based on repeated measurements of standard sialic acid in batches. Pure sialic acid (Sigma Chemicals) of known concentration was used to plot standard curve at 549 nm using established protocol of Thiobarbituric Acid Assay Method of Warren (FIG. 2). A comparison of sialic acid measurement by Warren's and Horgan's (Horgan I. E. Clin Chem Acta 116: 409–415 1981) method revealed that Horgan's method can also give reproducible and stable color development. The extinction coefficients of the color using Warren's and Horgan's method were 57,000 and 63,000 respectively, and the intra and inter assay coefficients of variations were 3.265 and 2.84%, respectively. Using Warren's method, human serum transferrin and plasma Apo J sialic acid contents were determined after acid hydrolysis. Varying the time of acid hydrolysis did not effect the amount of sialic acid in Apo J as determined by Warren's method. The amount of sialic acid in Apo J in a healthy non-drinking control subject was found to be 400 pmoles/μg protein, which is equal to 28 moles of sialic acid per mole of Apo J. Enzymatic hydrolysis of Apo J with bacterial neuraminidase (Sigma) led to incomplete hydrolysis resulting in only 70% of the expected value and thus is less preferred.

EXAMPLE III

Validity of Plasma SDJ as a Specific Marker for Chronic Alcohol Intake (Animal Model)

A group of Wistar male rats (approximately 150 g body wt.) was divided into experimental and control groups of 18 each and pair-fed their respective liquid diets. Six animals from each group were euthanized at 4, 6 and 8 weeks by exsanguination under pentobarbital anesthesia (50 mg/kg, ip). Blood plasma was collected from each animal. One ml of plasma from each sample was processed for HDL isolation. Apo J was purified from the HDL fraction by affinity chromatography as described above. The purified Apo J fraction was then chemically hydrolyzed with the 0.1 N sulfuric acid and sialic acid content in the fraction was measured as described above. Protein content of Apo J fractions was measured by the Pierce protein assay method. Smith et al., Anal. Biochem. 150: 76–85 (1985). The results are expressed as mole sialic acid/mole Apo J. The results are shown below and group comparisons were made by one way ANOVA followed by Tukey's test:
Effect of Chronic Ethanol on Sialic Acid Content of Rat HDL-Apo J

|  | Sialic acid (p moles/μg Apo J protein) | | |
| --- | --- | --- | --- |
| Group | 4 weeks | 6 weeks | 8 weeks |
| CN | 353 ± 11 | 350 ± 13 | 360 ± 12 |
| AN | 349 ± 7 | 266 ± 12 | 200 ± 17 |
| Percent decrease | 1.96 | 24.0 | 44.4 |
| P value | NS | <0.05 | <0.05 |

Figure 3:
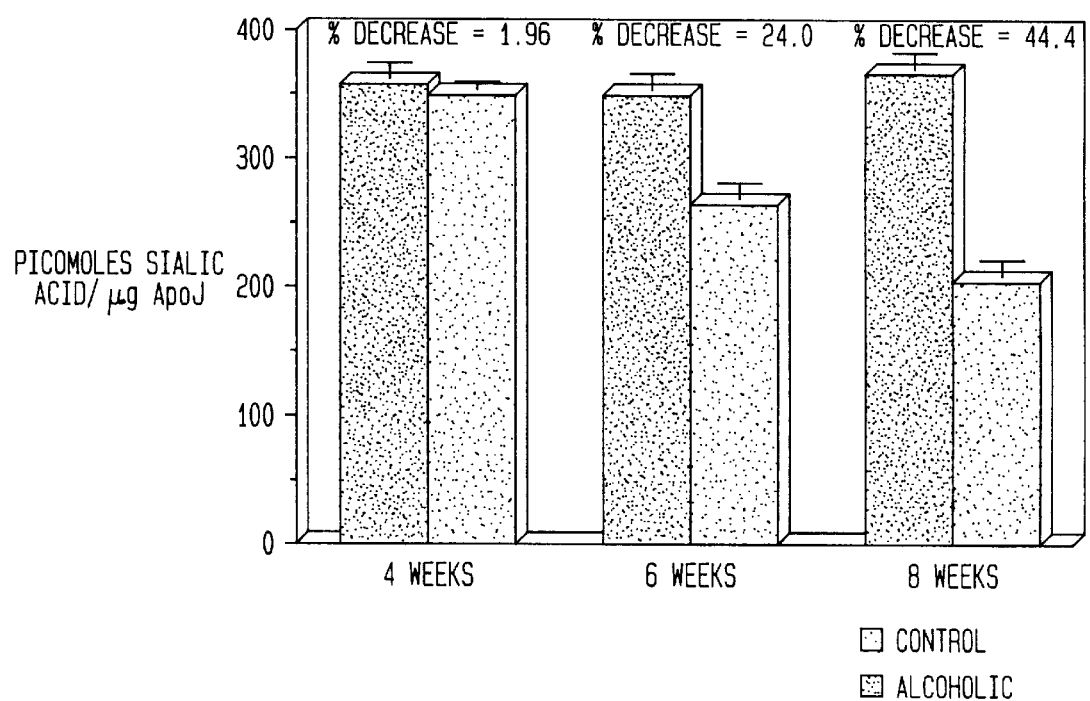
FIG. 3. is a bar graph which shows a gradual loss of sialic acid residues from Apolipoprotein J with increased duration of alcohol intake in rats.

The results are also shown in FIG. 3. These results show that Apo J, like other N-glycosylated protein is susceptible to deleterious action of chronic ethanol resulting in a significant 24% and 44% loss in sialic acid content, respectively, in 6 weeks and 8 weeks of feeding ethanol diet. No difference was observed when rats were fed their respective diets for only 4 weeks. The severity of the loss of sialic acid residue from Apo J molecule was shown to be directly related to the duration of ethanol administrated to rats.

EXAMPLE IV

Effect of Ethanol Concentration

Three groups of 6 Wistar male rats/group were maintained for 8 weeks on the following alcohol containing liquid diets (ethanol calories as % of the total dietary calories) or the corresponding isocaloric control liquid diets (where ethanol calories were replaced by isocaloric dextrin-maltose): (a) 12%, (b) 24% and (c) 36%. The animals in each group of control diet were pair-fed with the corresponding group on alcohol diet. After 8 weeks, all the animals were killed by aortic exsanguination under pentobarbital anesthesia (50 mg/kg, ip) and the plasma analyzed for the sialic acid content of affinity purified Apo J as described above. The results are shown below and group comparisons were made by one way ANOVA followed by Tukey's test. It can be seen from the table that there was an alcohol concentration dependent decrease in sialic acid content of plasma Apo J. This further strengthens our concept that the changes in Apo J sialic acid are not only dependent on the duration but also on the concentration of alcohol exposure.
Molar Ratio of Sialic Acid/Apolipoprotein J in Rats fed with Ethanol Containing Diet for Eight Weeks

| Dietary Ethanol | Mole Sialic acid/Mole Apo J | | |
| --- | --- | --- | --- |
| (as % of total Calories) | Alcohol group | Control group | P value |
| 12 | 19.2 ± 3.2 | 25.7 ± 3.8 | <0.05 |
| 24 | 17.2 ± 3.6 | 28.8 ± 3.8 | <0.05 |
| 36 | 14.1 ± 1.8 | 25.1 ± 3.2 | <0.05 |

EXAMPLE V

Disappearance of SDJ from Plasma after Abstinence from Alcohol Intake

Twenty Wistar male rats maintained for 8 weeks on the alcohol liquid diets as described above. At 8 weeks, all the animals were switched to the control liquid diet in a gradual manner over a one-week period (to avoid any ethanol withdrawal effects). At 1, 2, 3 and 5 weeks after they were on the control diet (0% alcohol) 5 animals/time point were killed and plasma analyzed for Apo J sialic acid. Group comparisons were made by one way ANOVA followed by Tukey's test and the results are shown below:
Molar Ratio Sialic Acid/Apolipoprotein J in Rats Withdrawn from an Eight Week Feeding with a 4.5% Ethanol Containing Diet

| weeks of withdrawal | Sialic acid/Apo J Mole/mole | P value |
| --- | --- | --- |
| 1 | 22.7 ± 2.7 | <0.05 |
| 2 | 25.8 ± 2.6 | <0.05 |
| 3 | 26.8 ± 3.1 | NS |
| 5 | 29.2 ± 4.0 | NS |

EXAMPLE VI

Effect of Storage of Plasma on Apo J Concentration of HDL and HDL Subclasses

Plasma samples collected from 10 male volunteers (Veterans Affairs Medical Center, Washington, D.C.) were stored either at 4° C. or at −20° C. for 4, 7 or 30 days. All precipitations of HDL were carried out in duplicate or triplicate and duplicate analyses of Apo J were performed by ELISA. The results not shown suggest that plasma can be stored at −20° C. at least for 30 days without affecting the recovery of Apo J, but not at 4° C. because Apo J recovery may be affected and that $HDL_3$ is more likely to be destroyed.

EXAMPLE VII

Plasma Apo J Sialic Acid Concentration in Human Drinkers and Non-drinkers: Effect of Liver Damage Plasma samples from 6 moderate drinkers (40 g alcohol/day for 16 months or longer) and 6 non-drinkers were processed for affinity column purification of Apo J. As shown below, the plasma Apo J sialic acid is decreased by 30% even in chronic moderate drinkers compared with non-drinkers. The sialylation index of Apo J is progressively reduced as the liver degenerates from fatty liver state to necrosis state.

Plasma Apo J Sialic Acid in Drinker and Non-drinkers

| PLASMA APO J SIALIC ACID IN DRINKER AND NON-DRINKER | | | |
|---|---|---|---|
| Plasma Component | Drinkers | Non-Drinkers | P value |
| Apo J Sialic acid (mole/mole) | 20.0 ± 2.3 | 28.8 ± 3.2 | <0.05 |

| Group | Patients | Sialylation Index | % normal |
|---|---|---|---|
| | Controls 8 | 28 | |
| FATTY LIVER | Alcoholic 6 | 14 | 50 |
| CIRRHOSIS | Alcoholic 4 | 9 | 32.1 |
| PRIOR TO LIVER TRANSPLANT | Alcoholic | 3 | 10.7 |

EXAMPLE VIII

Composition of HDL Subclasses, Apo J and Apo J Sialic Acid Levels from Healthy Males and Females Twenty healthy subjects (10 men and 10 women) voluntarily donated blood for this study at the Holy Cross Hospital in Silver Spring, MD. These subjects were healthy subjects without any known medical complications. After obtaining informed consent, fresh blood was collected in EDTA coated tubes and plasma was separated by low speed centrifugation. Plasma $HDL_2$ and $HDL_3$ were separated by dextran sulfate precipitation (1.43 g/dl) and characterized by SDS-PAGE analysis. Protein content and cholesterol content were determined by automated laboratory testing. Pure Apo J was isolated by passing the combined plasma HDL fractions through an anti-human Apo J-Sepharose 4B affinity column. Apo J levels were determined by ELISA. Pure Apo J fractions were further acid hydrolyzed to release sialic acid. The sialic acid was determined spectrophotometrically using an established protocol. The results obtained showed higher levels of HDL proteins and cholesterol in females as compared to their male counterparts. Apo J levels were also found to be higher in females as compared to males. However, the molar ratio of sialic acid content to that of Apo J protein remained the same in both male and female subjects. The results support using Apo J sialic acid as a tool for various diagnostic purposes.

| Total Protein, Apo J and Cholesterol Levels in Healthy Men and Women | | | |
|---|---|---|---|
| Parameters | | Men | Women |
| Protein | $DHL_2$ | 30.6 ± 1.2 | 36.4 ± 2.3 |
| | $HDL_3$ | 48.8 ± 2.8 | 55.6 ± 4.3 |
| Total Cholesterol | Plasma | 185 ± 34 | 192 ± 27 |
| | $HDL_2$ | 14.8 ± 0.9 | 21.2 ± 1.2 |
| | $HDL_3$ | 32.6 ± 4.7 | 38.3 ± 3.8 |
| HDL Apo J | | 14.6 ± 0.9 | 18.4 ± 2.6 |
| Sialic acid/Apo J | | 28.0 ± 0.8 | 28.0 ± 0.09 |

All values are expressed as mg/dl plasma except sialic acid/Apo J* which is expressed as moles sialic acid/mole of Apo J protein.

EXAMPLE IX

CDT vs Apo J. Utility of Loss of Sialic Acid of Plasma Apo J as Biological Marker For Alcohol Intake A group of 5 alcohol-dependent (50–60 g/day) and 4 non-drinking volunteer subjects in out-patient treatment at the University of Maryland Medical Center, Baltimore, MD were included in a study for a period of 4 weeks. On each day of their visit, the subjects were queried as to their alcohol intake, and their plasma levels of carbohydrate-deficient transferrin (CDT) and sialic-acid-content of Apo J were analyzed. The majority of the patients reported an excessive and fairly constant alcohol intake during the observation period (85–90 g/day). Of the 5 alcohol-consuming subjects, only 3 subjects showed a significant average increase of 7.3% (p<0.05) in their CDT levels at the end of 4 weeks. When the plasma of the same patients were analyzed for sialic acid content of Apo J, all but 1 patient showed an average increase of 14.3% (p<0.05) in the loss of sialic acid from plasma Apo J. The results indicate that the loss of sialic acid from Apo J responds to changes in alcohol intake in alcohol-dependent patients with higher sensitivity than CDT and may thus be useful as an efficient marker of alcohol intake.

| Plasma CDT And Apo J Sialic Acid Measured In Patients And Controls During The 4-Week Study | | | | | |
|---|---|---|---|---|---|
| | Alcohol | CDT (Units/liter) | | Sialic acid of Apo J (moles/mole protein) | |
| Time | intake | Patients | Controls | Patients | Controls |
| Day 0 | 50–60 g/day | 33.5 ± 4.8 | 20.5 ± 1.6 | 14 ± 1 | 28 ± 3 |
| Day 30 | 85–90 g/day | 35.9 ± 3.3 | 20.6 ± 1.2 | 12 ± 1 | 28 ± 3 |

Plasma CDT is expressed as units/liter based on the test kit from Kabi Pharmacia Diagnostics, Uppsala, Sweden.

EXAMPLE X

Determination of Sialic Acid in Plasma Apo J of Alcoholic Patients Undergoing Detoxification A study on alcoholic patients undergoing detoxification at the Substance Abuse Center at Providence General Hospital in District of Columbia was conducted. The study involved 11 out-patient subjects under the following categories: Group 1: Alcoholic patients admitted on day 0 (N=3); Group II: alcoholic patients undergone detoxification for 2 weeks (N=2); Group III: alcoholic patients undergone detoxification for 3 months (N=3); and Group IV: alcoholic patients with no alcohol intake for 6 months (N=3). The subjects were requested to donate blood after signing informed consent. At the start of the program, these patients were diagnosed as clinical alcoholics based on self-reporting, routine laboratory testing including liver enzymes, prothrombin time, albumin, total blood count, plus CDT measurements. The plasma collected from these patients were analyzed for Apo J sialic acid content. The patients of Group 1 showed on an average a 50% ($p<0.05$) loss of sialic acid in Apo J when compared to normal levels in non-drinkers. No recovery of Apo J sialic acid content was found in patients of Group II. However, patients of Groups III and IV showed a partial recovery, respectively, to an average of 60% ($p<0.05$) and 82.1% ($p<0.05$) of their sialic acid content of Apo J as compared to normal human Apo J sialic acid value. The results indicate that the sialic acid content of plasma Apo J may be used as a monitoring tool for patients undergoing detoxification in alcohol abuse treatment.

Apo J Sialic Acid Content of Alcoholic Patients Undergone Detoxification

| Group | Sialic acid Content of Plasma Apo J (moles/mole) of protein) | Percent of normal value |
| --- | --- | --- |
| Control | 28 ± 4 | — |
| Group I (N = 3) | 14 ± 2 | 50.0 |
| Group II (N = 2) | 14 ± 3 | 50.0 |
| Group III (N = 3) | 17 ± 2 | 60.7 |
| Group IV (N = 3) | 23 ± 2 | 82.1 |

EXAMPLE XI

Preparation of Anti Apo J Affinity Columns

Anti-Apo J affinity columns were prepared by dissolving IgG fractions of anti-Human Apo J in a minimum volume of coupling buffer (0.1 M NaHCO3, pH 8.3, containing 0.5M NaCl) and dialyzing extensively against the same buffer. Cyanogen bromide activated Sepharose 4B, (LKB-Pharmacia, about 4 g dry wt) is swollen and washed with 1 mM HCl were mixed end over end with about 10 mg of Anti-Apo J in 12 ml final volume of the coupling buffer for 2 hours at room temperature (RT) followed by mixing at 4° C. overnight.

The matrix was washed with the coupling buffer over a sintered glass funnel and resuspended in 12 ml of 1 M ethanolamine, pH 9, and mixed end over end for another 2 hours at room temperature. The matrix was filtered and washed (3 cycles) alternately with 0.1 M acetate buffer, pH 4 containing 0.5 M NaCl and 0.1 M Tris buffer, pH 8 containing 0.5 M NaCl. Finally, the Sepharose 4B affinity matrix containing the ligand of Anti-human Apo J was stored at 4° C. The percent IgG bound to the column was determined to assure proper column qualification. The column exhibited a minimum of 75% binding of the IgG.

A small column of anti-human Apo J was equilibrated with 0.025 M sodium bicarbonate buffer, pH 7.4 (elution buffer) or other suitable buffers. Typical sample processing, involved 200 μg of human HDL protein treated with 10 mM sodium decyl sulfate and transferred to the Anti-human Apo J column. The column was washed initially with 30 ml 0.025 sodium bicarbonate followed by 20 ml sequential washes with 0.5 M, 0.75 M, and 1 M sodium bicarbonate buffers. The Apo J protein was eluted in the fractions with 0.5 M bicarbonate strength. To qualify the affinity column and confirm the elution profile, a SDS-Page and/or an Ouchterlony analysis of these fractions against anti-human Apo J may be conducted to rule out any possible cross-reactivity with Apo A, Apo E or Albumin. This column validation is an indicator that this Anti-human Apo J column facilitates the selective binding of Apo J and its purification from other plasma proteins.

All publications mentioned in this specification are indicative of the level of skill of those skilled in the art to which this invention pertains. All these publications are herein incorporated by reference to the same extent as if each individual publication was specifically and individually indicated to be incorporated by reference.

Various modifications of the invention described herein will become apparent to those skilled in the art. Such modifications are intended to fall within the scope of the appending claims.

Financial support, in part, for the invention described herein was received from the National Institute of Health under cooperative agreement No. AA11038. Therefore, the U.S. Government may have certain rights in the invention.

What is claimed is:

1. A method for quantifying chronic alcohol use, comprising:
 a) obtaining at least one sample containing Apolipoprotein J (Apo J) from a subject;
 b) quantifying the number of Apo J molecules in said sample;
 c) quantifying the number of Apo J bound sialic acid molecules in said sample;
 d) calculating a sialylation index of said sample by determining the average number of molecules of Apo J bound sialic acid per molecule of said Apo J in said sample;
 e) comparing said sialylation index of said sample with the sialylation index of subjects that do not drink alcohol; and
 wherein a decrease in the sialylation index is indicative of chronic alcohol use.

2. The method in claim 1, wherein said Apo J is extracted from said sample to obtain a purified ApoJ sample prior to the quantifying of the number of molecules of said Apo J and Apo J bound sialic acid in said sample.

3. The method in claim 2, wherein said Apo J bound sialic acid is extracted from said purified Apo J sample to obtain a sialic acid free, purified Apo J containing portion and a sialic acid containing portion, that is derived from said purified Apo J sample, prior to the quantifying of the number of said Apo J and said Apo J bound sialic acid molecules in said sample.

4. The method of claim 1, wherein said sample is blood.

5. The method of claim 1, wherein said sample is plasma.

6. The method of claim 1, wherein said sample is serum.

7. The method of claim 1, wherein said sample comprises high-density lipoproteins (HDL).

8. The method of claim 2, wherein said purified Apo J sample is obtained by contacting said sample with a matrix having immobilized; thereon, antibodies that bind Apo J.

9. The method of claim 8, wherein said antibodies are monoclonal.

10. The method of claim 8, wherein said antibodies are anti-Apo J monoclonal antibodies.

11. The method of claim 3, wherein said Apo J bound sialic acid is extracted from said purified Apo J sample to obtain said sialic acid free purified Apo J containing portion and sialic acid containing portion, derived from said purified Apo J sample, by subjecting said purified Apo J to hydrolysis prior to the quantifying of the number of said Apo J and said Apo J bound sialic acid molecules in said sample.

12. The method of claim 11, wherein said hydrolysis is conducted enzymatically.

13. The method of claim 11, wherein said hydrolysis is conducted chemically by an acid.

14. The method of claim 13, wherein said acid hydrolysis comprises reacting said purified Apo J with sulfuric acid.

15. The method of claim 1, wherein samples are taken from one subject over a period of time and a sialylation index is calculated for each of said samples; whereby multiple sialylation indexes are examined to determine the trend and rate of change of the sialylation index over time; and thereby determining the trend and rate of change in chronic alcohol use over time.

16. A kit for measuring an Apo J sialylation index, comprising:

a) a matrix having immobilized thereon;

b). antibodies that bind Apo J; and c) a desialylation agent.

17. The kit of claim 16, wherein said matrix is contained in a column.

18. The kit of claim 16, wherein said desialylation agent is sulfuric acid.

19. The kit of claim 16, further comprising purified Apo J.

* * * * *